(12) United States Patent
Borm et al.

(10) Patent No.: US 11,596,774 B2
(45) Date of Patent: Mar. 7, 2023

(54) GUIDE WIRE FOR MINIMALLY INVASIVE OPERATIONS AND METHOD FOR PRODUCING A GUIDE WIRE

(71) Applicant: Nano4Imaging GmbH, Aachen (DE)

(72) Inventors: Paul J. A. Borm, Meerssen (NL); Christoph R. Manegold, Dusseldorf (DE); Jozef G. O. Cremers, Heerlen (NL)

(73) Assignee: NANO4IMAGING GMBH, Düsseldorf (DE)

( * ) Notice: Subject to any disclaimer, the term of this patent is extended or adjusted under 35 U.S.C. 154(b) by 490 days.

(21) Appl. No.: 16/623,107

(22) PCT Filed: May 29, 2018

(86) PCT No.: PCT/EP2018/064118
§ 371 (c)(1),
(2) Date: Dec. 16, 2019

(87) PCT Pub. No.: WO2018/228817
PCT Pub. Date: Dec. 20, 2018

(65) Prior Publication Data
US 2021/0187253 A1 Jun. 24, 2021

(30) Foreign Application Priority Data
Jun. 16, 2017 (EP) .................... 17176412

(51) Int. Cl.
*A61M 25/09* (2006.01)
*A61M 25/01* (2006.01)
(Continued)

(52) U.S. Cl.
CPC ........ *A61M 25/09* (2013.01); *A61M 25/0127* (2013.01); *B29C 65/02* (2013.01);
(Continued)

(58) Field of Classification Search
CPC ..... B29C 66/73715; A61M 2025/0915; A61M 2025/09175; A61M 2025/09108; A61M 2025/09133
See application file for complete search history.

(56) References Cited

U.S. PATENT DOCUMENTS 8,292,828 B2 10/2012 Uihlein
2003/0060731 A1* 3/2003 Fleischhacker ....... A61M 25/09
600/585
(Continued)

FOREIGN PATENT DOCUMENTS

| DE | 102005022688 A1 | 11/2006 |
|---|---|---|
| EP | 2098262 A1 | 9/2009 |
| EP | 2548604 A1 | 1/2013 |

OTHER PUBLICATIONS

International Search Report from International Application No. PCT/EP2018/064118 dated Aug. 22, 2018.

*Primary Examiner* — Carson Gross
(74) *Attorney, Agent, or Firm* — Brundidge & Stanger, P.C.

(57) ABSTRACT

A guide wire for minimally invasive operations with a distal wire end piece (3, II) connected to a wire main piece (2), wherein the guide wire (I, 10) has, at least in the distal wire end piece (3, II), an inner shaft (4, 14) and at least one protective layer enclosing the inner shaft (4, 14), the inner shaft (4, 14) comprises a first fibre composite material and, at least in the distal wire end piece (3, II), the inner shaft (4, 14) has a plurality of weakened points (8, 18), which are created by mechanical interventions, is characterised in that the weakened points (8, 18) are created by buckling load, bending load and/or breaking load. Correspondingly, for a method for producing a guide wire of this kind it is proposed that the weakened points (8, 18) are created by buckling load, bending load and/or breaking load.

33 Claims, 2 Drawing Sheets

Figure 1:
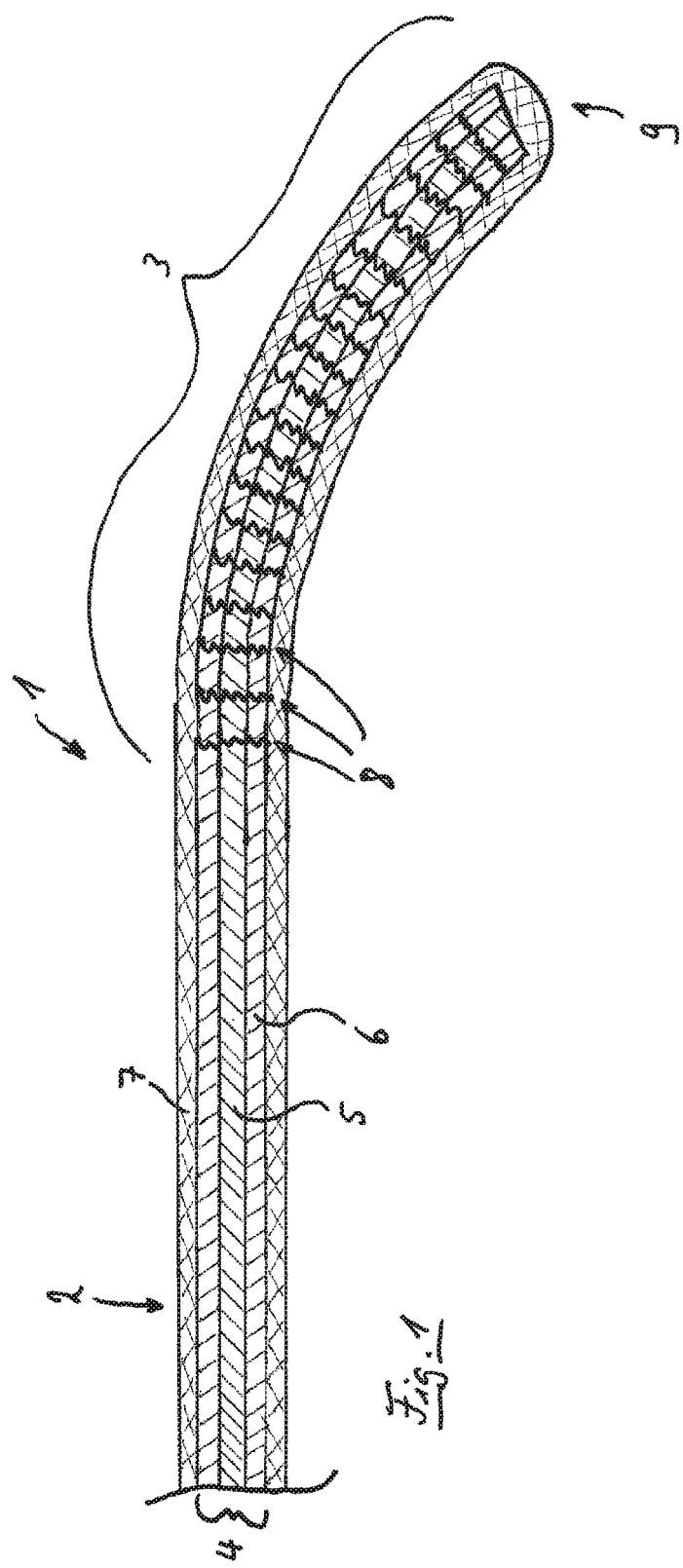

(51) Int. Cl.
  *B29C 65/02*   (2006.01)
  *B29C 70/84*   (2006.01)
  *B29C 65/00*   (2006.01)

(52) U.S. Cl.
  CPC ........ *B29C 66/73715* (2013.01); *B29C 70/84* (2013.01); *A61M 2025/09083* (2013.01); *A61M 2025/09108* (2013.01); *A61M 2025/09133* (2013.01)

(56) References Cited

U.S. PATENT DOCUMENTS

2004/0167438 A1   8/2004   Sharrow
2008/0312597 A1   12/2008  Uihlein
2014/0121648 A1   5/2014   Weiss \* cited by examiner

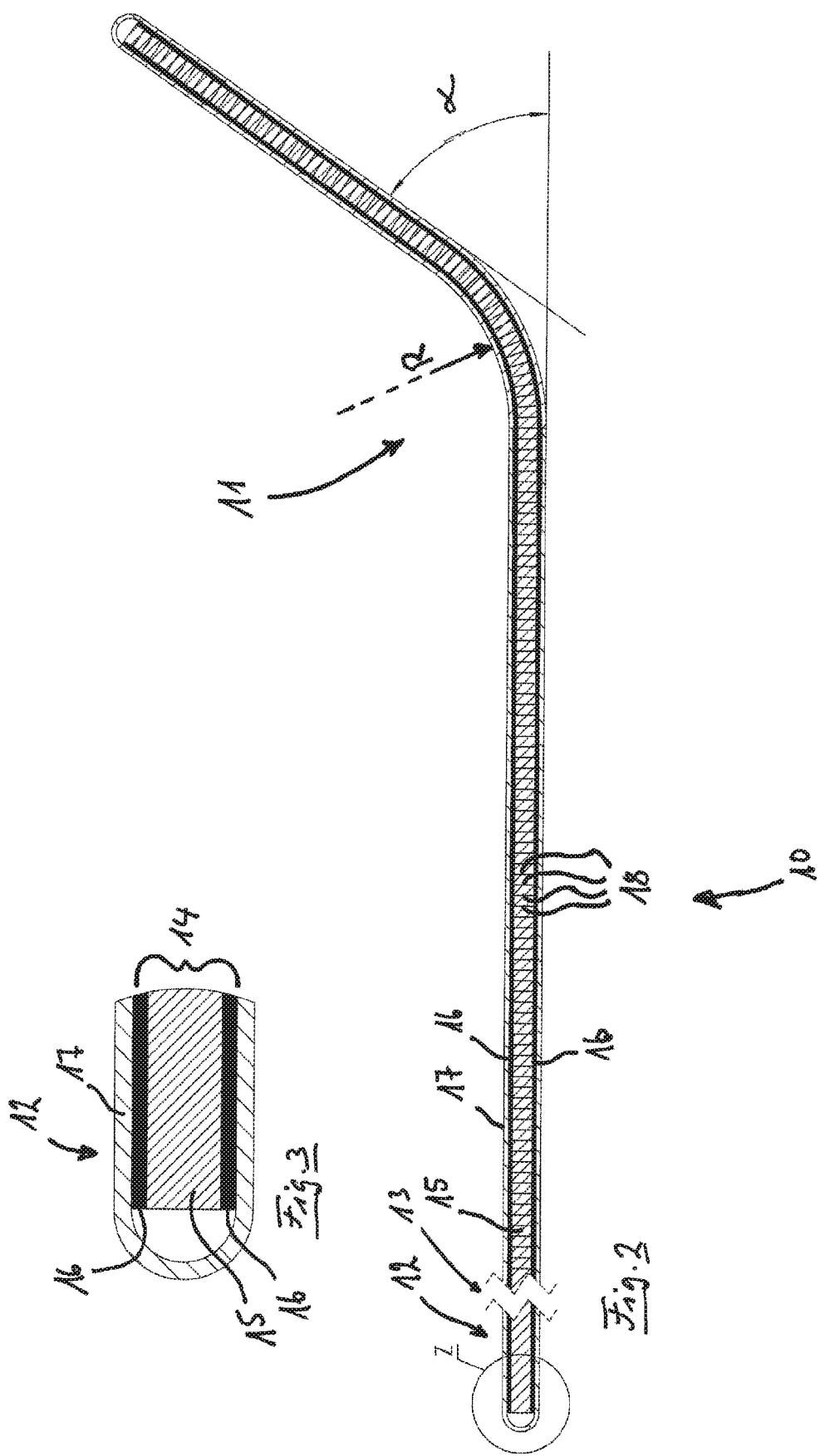

GUIDE WIRE FOR MINIMALLY INVASIVE OPERATIONS AND METHOD FOR PRODUCING A GUIDE WIRE

The invention relates to a guidewire according to the preamble of claim 1 and to a method for producing a guidewire according to the preamble of claim 15.

EP 1 348 461 B1 discloses a guidewire in which an inner shaft of the guidewire made of a metal or of a plastic with a relatively high degree of stiffness is surrounded by a plastic layer. At the distal wire endpiece of the guidewire, the core is tapered conically in order to obtain a greater degree of flexibility of the wire endpiece.

US 2014/0121648 A1 discloses a guidewire with a tapering at the distal end of a core made of a composite material, wherein the tapering is intended to increase the flexibility of the wire endpiece. The shaping of the core tip is carried out by grinding or cutting.

US 2004/0167438 A1 likewise discloses a guidewire with a tapering at the distal end of a core, wherein the tapering of the core can be provided in several steps. Here too, the shape of the core tip is intended to obtain desired mechanical properties, e.g. as regards the flexibility of the wire endpiece.

EP 2 098 262 A1 discloses a catheter guidewire with a core, in the basic material of which twisted fibers, preferably glass fibers, are embedded, and of which the distal wire endpiece can have a tapering shape generated by grinding.

DE 10 2005 022 688 A1 likewise discloses a guidewire with a core tapered at the distal end.

Depending on the production method for the core of a guidewire, a reduction of the diameter of the core is complicated, regardless of whether it is provided conically or in steps. In particular, grinding methods are time-consuming and costly.

EP 2 547 604 A1 discloses a guidewire and method of the types mentioned at the outset. The guidewire has a core which also extends into a distal wire endpiece and which has randomly distributed non-metallic fibers or fiber segments and a resin filling the spaces between the fibers. In one illustrative embodiment, the core has radially oriented incisions on its circumference, which are intended to make the distal wire endpiece more flexible. The incisions can be generated by cutting or etching. The depth or width of the incisions or the distance between the incisions can be adapted according to the desired flexibility.

The technical problem addressed by the invention is to make available a guidewire having a higher degree of flexibility in a wire endpiece, and also a method for production of said guidewire, wherein the distal wire endpiece of the guidewire has an alternative structure to the prior art, and one that is easier to produce.

In the case a guidewire of the type mentioned at the outset, the technical problem is solved by the characterizing features of claim 1. In the case of a method of the type mentioned at the outset, the technical problem is solved by the features of claim 15. Advantageous embodiments of the invention are set out in the dependent claims.

Accordingly, it is proposed that an inner shaft, at least in a distal wire endpiece, has a multiplicity of weakened sites which are generated by mechanical interventions, namely by buckling loads, bending loads and/or breaking loads.

The weakened sites reduce the flexural stiffness of the inner shaft and thus of the distal wire endpiece, that is to say its flexural modulus is reduced. With the reduced flexural stiffness, the flexibility of the guidewire increases, as does its ability to follow curved trajectories.

The breaking, buckling or bending acts on the entire cross section of the core, without causing complete separation of the core. In particular, the fine fibers of the fiber composite material are at least in part not separated by the bending, buckling or breaking movement and, despite the weakening, cause the core to hold together. The breaking, buckling or bending for introducing the weakened sites can additionally save considerably on costs and time compared to the incising or etching of the weakened sites into the inner shaft, as is known from the prior art.

The number of weakened sites depends in particular on the length of the distal wire endpiece. Thus, the distal wire endpiece can measure 10 mm to 50 mm, for example. Shorter or longer distal wire endpieces are likewise possible. The weakened sites are preferably at regular distances from each other in the axial direction of the guidewire.

The distances between the weakened sites are preferably in the millimeter range. Preferably, a distal wire endpiece can have weakened sites over a length of 30 to 60 mm, preferably 40 mm, which weakened sites are preferably spaced apart from each other by approximately 1 mm to 3 mm, e.g. 2 mm+/−0.5 mm. For the production of the distal wire endpiece, a method is proposed in which the inner shaft provided at least in the distal wire endpiece is provided, by mechanical intervention, with a multiplicity of weakened sites, wherein the weakened sites are generated by buckling loads, bending loads and/or breaking loads.

The method according to the invention can be carried out in particular such that, for the mechanical interventions, the inner shaft is placed over at least one mechanical edge and is subjected to a force acting transversely with respect to the longitudinal axis of the unweakened wire endpiece. For example, the inner shaft can be placed over the mechanical edge, and the force can act on a part of the inner shaft protruding beyond the edge. To generate the successive weakened sites, the inner shaft merely needs to be advanced by a suitable distance, e.g. by a distance length of 1 mm to 3 mm. The force can be the weight force of a mass fixed to the inner shaft, e.g. by clamping.

The method according to the invention can be such that the mechanical interventions are carried out in at least two different rotation angle positions of the inner shaft. The rotation angle position relates to a rotation about the longitudinal axis of the inner shaft. For example, the inner shaft can be made weaker at a multiplicity of weakened sites without rotating it about its longitudinal axis. Thereafter, the inner shaft can be rotated about the longitudinal axis by a defined rotation angle, e.g. of 90° or in a range of 80° to 100°, relative to the acting force, in order thereafter to introduce further weakened sites in the region already weakened in the first pass or to further weaken already existing weakened sites. In this way, it is ensured that the weakening the flexural stiffness of fiber composite material. Moreover, the at least one envelope layer or at least one of the envelope layers can advantageously have a second fiber composite material, wherein the second fiber composite material is preferably different than the first fiber composite material.

With the combination of core and envelope layer, desired mechanical properties of the inner shaft can be set. Thus, the two fiber composite materials can be the same as regards their materials, or they can differ in terms of the fiber material and/or in terms of the matrix material adhesively connecting the fibers to one another or enveloping them. The matrix material can be a resin, for example synthetic resin, in particular epoxy resin, or some other plastic.

The fibers of the envelope layer, at least a subset of said fibers, are preferably guided helically about the circumference of the core. Helical guiding of the fibers signifies that they do not extend continuously in the axial direction but instead surround the core in the shape of a helix. The helical guiding of the fibers ensures an increased torsional stiffness in particular outside the region provided with the weakened sites, i.e. ensures improved transmission of torques. Outside the region provided with weakened sites, the flexural stiffness can be defined substantially by the core with its fibers adhesively bonded to one another by the matrix material of the core.

In the distal wire endpiece, by contrast, the flexural stiffness can be reduced to a desired extent by the introduction of the weakened sites, wherein the degree of reduction of the flexural stiffness can be influenced by the given density of the weakened sites in the axial direction.

Preferably, at least a subset of the fibers are guided in at least two different helical orientations about the circumference of the core, such that the torsional stiffness is increased for both circumferential directions. The fibers of the envelope layer are encased by a matrix material and/or adhesively bonded to one another by means of the matrix material. The matrix material can be a resin, for example synthetic resin, or some other plastic. The matrix material can be the same matrix material as that of the core or can be another matrix material.

In the core, at least a plurality of the fibers are preferably oriented in the axial direction of the guidewire.

For the fibers of the inner shaft, it is possible, for example, to use non-conductive fiber materials, e.g. made of plastic and/or inorganic materials. Non-conductive materials are particularly advantageously used in MRT. Suitable plastics for the fibers may be, for example: glass, nylon (polyamide), polyester, PEEK, polyacryl, ultra-high molecular weight polyethylene (UHMWPE), liquid crystal polymers (LCP), aramids. Polymer optical fibers (POF) can also be used. In the case of a structure of the inner shaft composed of core and envelope layer(s), these fiber materials can be used both for the core and also for the at least one envelope layer. Preferably, glass fibers are used in the core and an aramid in the envelope layer of the inner shaft.

The guidewire according to the invention can preferably be configured, by the method according to the invention, such that at least one marking element serving for marking purposes in an imaging method is applied to the outer circumference of the inner shaft.

In this way, the profile of the guidewire can be monitored during use. The at least one marking element or at least one of the marking elements is preferably an MRT marking element which is suitable for marking in magnetic resonance tomography and which has at least one marking agent which, during use in a magnetic resonance tomography (MRT) apparatus, is visible on account of its interaction with the electromagnetic alternating fields of the MRT. The marking agent is preferably one that generates a positive contrast, more preferably one that reduces the T1 relaxation time and/or the T2 relaxation time. These include, for example, the salts of the lanthanides $GD^{3+}$, $Ho^{3+}$, $Dy^{3+}$, $Eu^{3+}$, the complexes of some transition metals, e.g. $Fe^{3+}$, $Mn^{2+}$, $Mn^{3+}$ and $Co^{3+}$. Such agents permit visibility of the medical instrument in the current MRT methods without special measures. Further agents, including those that generate positive or negative contrasts in other imaging methods, e.g. MPI (magnetic particle imaging) or in methods using X-rays, can likewise be provided.

At least one active marking element can also be used, alone or in addition to passive marking elements. Active means that the marking element not only passively influences an electrical or magnetic field, and therefore the imaging, but actively emits an electrical and/or magnetic field, in particular an alternating field. For this purpose, the active marking element can have, for example, a coil, in particular a high-frequency coil (HF coil). The active marking element can be supplied with voltage through fine conducting wires extending through the guidewire. However, for operation in MRT, it is advantageous to dispense with such wires. The active marking element can also be powered by means of induction from the alternating field of the magnetic resonance tomography apparatus or another external source of an alternating field.

The guidewire according to the invention can also be configured such that the at least one marking element is applied externally to the envelope layer. The marking element can be applied, for example, in a printing method, i.e. by being printed on. This procedure can also be provided in the case of an active marking element.

The at least one marking element preferably forms a ring enclosing the envelope layer. In the case of a plurality of marking elements, they can be at defined distances from one another as seen in the axial direction of the guidewire. These distances can be uniform. However, it is also conceivable to vary the distances and use these as indexing means for defined positions of the guidewire. Alternatively or in addition, indexing can be provided by varying the length of the marking elements in the longitudinal direction of the guidewire. Moreover, alternatively or additionally, different marking elements can have different concentrations of the marking agent.

The guidewire according to the invention can also be configured such that the protective layer surrounding the inner shaft is a protective jacket. In the case of several protective layers, the protective jacket forms the outermost layer. The protective jacket is preferably made of PTFE (polytetrafluoroethylene) or at least has PTFE, although it can also have one or more other plastics. The protective jacket is preferably applied directly to the inner shaft or, if the inner shaft is intended to be surrounded by further inner protective layers, the protective jacket is applied to the outermost of the inner protective layers, preferably by shrink-fitting. The use of special adhesives for fixing the protective jacket is thus omitted. Moreover, an adhesive is not needed for closing the guidewire at the ends, since the protective jacket can be already closed at the distal or proximal end, or the material of the protective jacket, particularly in the case of PTFE, can be welded at one or both ends. Moreover, a cohesively bonded connection between the protective jacket and the underlying layer, in particular the envelope layer, can be generated by the action of temperature.

Moreover, it can be advantageous to carry out the method according to the invention such that, before the protective jacket is shrink-fitted, the wire endpiece provided with the protective jacket is fixed in a shape-fixing device predefining the shape of the wire endpiece, and the protective jacket is shrunk on over the fixed wire endpiece. Through the shrink-fitting process, the wire endpiece remains stable in its predefined shape. In the shape-fixing device, the wire endpiece is preferably given a curved shape. The shape-fixing device can have, for example, a groove with the desired profile, into which groove the wire endpiece is placed before the shrink fitting of the protective jacket. The groove can be closed with a cover. Alternatively to a groove, the shape-fixing device can have a modifiable shape definer, e.g. by displaceable or plug-in limiting elements which, for example, can be pin-shaped.

Furthermore, it can be advantageous to configure the guidewire according to the invention, or to carry out the method according to the invention, in such a way that the guidewire has a free proximal wire endpiece which adjoins the end of the wire main piece opposite the distal wire endpiece. A free proximal wire endpiece affords a user the option of using the proximal wire endpiece as a guide tip too. The functions of the proximal wire endpiece and those of the distal wire endpiece can thus be changed around.

The free proximal wire endpiece and the distal wire endpiece can be designed corresponding to one another or can also be different. In the case of a different design, different properties, e.g. different flexibility or different shapes, can be obtained, which can be exploited during use.

It may be expedient to provide a multiplicity of weakened sites in the distal wire endpiece alone, such that the user has available a more flexible and stiffer wire endpiece. However, it is also possible for both wire endpieces to be provided with a multiplicity of weakened sites.

Furthermore, the proximal wire endpiece or the distal wire endpiece, or both wire endpieces, can be given a bent shape, preferably with a bending angle of at least 45° and at most 90°.

As in the distal wire endpiece, it is also possible for the proximal wire endpiece to have an inner shaft having a first fiber composite material and at least one protective layer enveloping the inner shaft. The wire main piece can also have such an inner shaft having a fiber composite material, and at least one protective layer enveloping the inner shaft. Inner shaft and protective layer are preferably at least substantially of the same material in the wire endpieces and the wire main piece and, apart from the weakened sites, are of at least substantially the same structure, such that the wire endpieces together with the wire main piece are in one part with a continuous core, continuous envelope layer and continuous protective layer. If necessary, however, weakened sites can also be provided in the wire main piece.

Finally, the at least one marking element already mentioned above can be applied at the distal wire endpiece, at the proximal wire endpiece or at both wire endpieces.

It may also be expedient to provide at least one marking element alone in the wire main piece or in the wire main piece and additionally at least one marking element in one or both of the wire endpieces.

The at least one marking element or at least one of the marking elements can be applied to the outer circumference of the inner shaft in the distal wire endpiece, in the proximal wire endpiece and/or in the wire main piece. The at least one marking element or at least one of the marking elements can also be an MRT marking element suitable for marking in magnetic resonance tomography, wherein preferably the at least one MRT marking element or at least one of the MRT marking elements is an active marking element.

Preferred embodiments of the guidewire according to the invention and of the production method according to the invention are set out below with reference to figures.

In the schematic figures:

FIG. 1 shows the front region of a first guidewire with a distal wire endpiece, FIG. 2 shows a second guidewire with a distal and a proximal wire endpiece, and FIG. 3 shows an enlarged detail from the proximal wire endpiece.

FIG. 1 shows the front region of a guidewire 1 with a wire main piece 2 and with a distal wire endpiece 3 seamlessly adjoining the latter. The first guidewire 1 has an inner shaft 4, which consists of a core 5 and of an envelope layer 6 surrounding the core 5. A protective jacket 7, preferably of PTFE, is pulled over the inner shaft 4 and shrink-fitted. To make matters clearer, the size ratios are not true to scale in the figure. The length of the wire endpiece 3 is in fact of the order of preferably 30 mm to 60 mm, and the diameter of the first guidewire 1 is of the order of less than 1 mm.

The core 5 consists of a fiber composite material which has glass fibers and, as plastic matrix, an epoxy resin. The glass fibers (not shown in the figure) are at least predominantly oriented in the longitudinal direction of the first guidewire 1. To produce the core, the glass fibers, which are preferably continuous over the length of the first guidewire 1, are provided with the plastic matrix in a pultrusion method.

The envelope layer 6 likewise consists of a fiber composite material, wherein fibers of an aramid are preferably used here. The fibers (not shown) are preferably wound helically in two different orientations about the core 5. Thereafter, the plastic matrix for the envelope layer 6 is applied, likewise in a pultrusion method. Preferably, the plastic matrix is likewise epoxy resin. The two pultrusion methods can be carried out during a common drawing process.

After the inner shaft 4 has been finished, it is provided in the distal wire endpiece 3, by mechanical intervention, with a multiplicity of weakened sites 8, of which only the rear three weakened sites 8, as seen from the distal end 9, are provided with the reference number in the figure. The weakened sites 8 serve to reduce the flexural stiffness of the guidewire 1 in the wire endpiece 3. The weakened sites 8 thus replace the much more complicated reduction of the diameter of the inner shaft 4, as known from the prior art.

In order to generate the weakened sites 8, the inner shaft 4 can be placed with its distal end over a mechanical edge (not shown here). On a part of the inner shaft 4 protruding beyond the mechanical edge, a force with a component perpendicular to the longitudinal direction of the inner shaft 4 is applied to the inner shaft 4. With sufficient force, this causes a movement of the inner shaft 4 with a bending, buckling and/or breaking load, which leads to formation of cracks in the inner shaft 4. Since in particular the glass fibers in the core 5 are largely not broken during said movement, the inner shaft 4 remains in one piece, and complete breaking-off of part of the inner shaft 4 can be avoided. The bending, buckling and/or breaking load leads instead to a partial tearing open of the plastic matrix, as a result of which the flexural stiffness of the inner shaft 4 is reduced considerably at the weakened site 8 that is generated.

The mechanical weakening is then repeated many times, for example by means of the inner shaft 4 being pushed farther out over the mechanical edge until the acting force generates the next weakened site 8. In a distal wire endpiece 3 with a length of 40 mm, for example, twenty weakened sites 8 are preferably formed at an interval of approximately 2 mm. However, the distal wire endpiece 3 can also have a length of 30 mm to 60 mm, for example, in which case the intervals between the weakened sites preferably measure 1 to 3 mm. The entire process can then be repeated with a modified rotation angle position of the inner shaft 4. For example, after the first pass for introducing a multiplicity of weakened sites 8, the inner shaft 4 is rotated about the longitudinal axis by approximately 90° relative to the direction of the acting force and is treated correspondingly in a second pass.

The acting force can be generated, for example, by means of the weight force of a mass (not shown here) fixed at the distal end of the inner shaft 4.

After the inner shaft 4 has been provided with the desired number of weakened sites 8, the protective jacket 7 is pulled over the inner shaft 4. Thereafter, at least the distal wire endpiece 3 is optionally brought to a desired shape and is fixed in a shape-fixing device (not shown here). Thereafter, the protective jacket 7 is shrink-fitted onto the inner structure 4 at a suitable temperature. After cooling, the shape of the wire endpiece 3 remains on account of the stabilizing effect of the shrink-fitted protective jacket 7, even after removal from the shape-fixing device. The conferred shape, at least in a subportion, is preferably an arc shape.

FIG. 2 shows a second guidewire 10 with a distal wire endpiece and a proximal wire endpiece 12. A wire main piece is not shown here and falls in the gap 13 in the depiction of the second guidewire 10. Apart from weakened sites explained below, the wire endpieces 11 and 12 have substantially a matching structure. A region of the proximal wire endpiece 12 marked "Z" in FIG. 2 is shown enlarged in FIG. 3. A core 15 of the second guidewire 10, an envelope layer 16 surrounding the core 15, and a protective layer in the form of a protective jacket 7 can be seen in the enlargement. Core 15 and envelope layer 16 together form the inner shaft 14. Thus, the second guidewire 10 corresponds in structure to the wire main piece 2 and the distal wire endpiece 3 of the first guidewire 1 according to FIG. 1. The distal wire endpiece 11 has, in the inner shaft 14, a multiplicity of weakened sites 18, which are symbolized by lines perpendicular to the longitudinal axis of the second guidewire 10, and of which only four are labeled with reference signs. The weakened sites 18 are distributed over the entire length of the distal wire endpiece 11 shown and result in an increased flexibility of the distal wire endpiece 11. The weakened sites can be produced in the same way as already described with reference to FIG. 1 or in another suitable way.

By contrast, in the illustrative embodiment in FIG. 2, the proximal wire endpiece 12 is formed without weakened sites. A user can decide whether to use the distal wire endpiece 11 or the proximal wire endpiece 12 as the tip of the second guidewire for guiding another instrument, e.g. a catheter (not shown here).

The distal wire endpiece 11 is bent in a subportion 19, wherein the bending angle α measures approximately 63°. The bending can be regular with a constant bending radius R or irregular with a changing bending radius R. The production of the bend and/or the application of the protective jacket 17 can also take place in the same way as already described with reference to FIG. 1 or in another suitable way.

LIST OF REFERENCE SIGNS 1 first guidewire
2 wire main piece
3 wire endpiece
4 inner shaft
5 core
6 envelope layer
7 protective jacket
8 weakened site
9 distal end
10 second guidewire
11 distal wire endpiece
12 proximal wire endpiece
13 gap
14 inner shaft
15 core
16 envelope layer
17 protective jacket
18 weakened sites
19 subportion
α bending angle
R bending radius

What is claimed is:

1. A guidewire device for minimally invasive interventions, the guidewire device comprising:
 a wire main piece; and
 a distal wire endpiece adjoining the wire main piece, wherein:
  the distal wire endpiece includes a first inner shaft and at least one protective layer enveloping the first inner shaft,
  the first inner shaft includes:
   a first fiber composite material,
   a plurality of weakened sites that are generated by mechanical interventions, a core, and
   a plurality of envelope layers surrounding the core,
  the core includes the first fiber composite material,
  the first fiber composite material includes glass fibers,
  at least one of the plurality of envelope layers includes a second fiber composite material, wherein the second fiber composite material includes aramid fibers being enveloped by a plastic matrix material, and
  the weakened sites are generated by at least one of: buckling loads, bending loads, or breaking loads.

2. The guidewire device of claim 1,
 wherein at least one subset of the aramid fibers of the second fiber composite material is guided helically about a circumference of the core.

3. The guidewire device of claim 2,
 wherein the at least one subset of the aramid fibers of the second fiber composite material is guided in two oppositely directed, different helical orientations about the circumference of the core.

4. The guidewire device of claim 1, wherein the protective layer or, in a case of more than one protective layer, an outermost protective layer is a protective jacket including PTFE.

5. The guidewire device of claim 1, wherein at least one marking element suitable for marking in an imaging method is incorporated in or attached to the guide wire device.

6. The guidewire device of claim 5, wherein the at least one marking element includes at least one magnetic resonance tomography (MRT) marking element suitable for marking in magnetic resonance tomography.

7. The guidewire device of claim 6, wherein the at least one MRT marking element includes an active marking element.

8. The guidewire device of claim 5, wherein at least one of a plurality of marking elements is applied to an outer circumference of the inner shaft.

9. The guidewire device of claim 1, further comprising a proximal wire endpiece adjoining an end of the wire main piece opposite the distal wire endpiece.

10. The guidewire device of claim 9, wherein the proximal wife endpiece comprises a second inner shaft, the second inner shaft having a second fiber composite material, and at least one protective layer enveloping the second inner shaft.

11. The guidewire device of claim 10, wherein the second inner shaft includes a plurality of weakened sites that are generated by mechanical interventions.

12. The guidewire device of claim 11, wherein the mechanical interventions include at least one of: buckling loads, bending loads, or breaking loads.

13. The guidewire device of claim 9, wherein at least one marking element is arranged in the proximal wire endpiece.

14. The guidewire device of claim 1, wherein a bent shape is conferred on at least one of: the distal wire endpiece or to a proximal wire endpiece.

15. The guidewire device of claim 14, wherein the bent shape has a bending angle ($\alpha$) of at least 45° and at most 90°.

16. A method for producing a guidewire for minimally invasive interventions, comprising:
    adjoining a distal wire endpiece to a wire main piece, wherein the distal wire endpiece includes a first inner shaft having a first fiber composite material; and
    providing, in the first inner shaft of the distal wire endpiece, a plurality of weakened sites generated by mechanical interventions, wherein the mechanical interventions include at least one of: buckling loads, bending loads, or breaking loads.

17. The method of claim 16, further comprising adjoining on the guidewire, a proximal wire endpiece which adjoins an end of the wire main piece opposite the distal wire endpiece.

18. The method of claim 17, further comprising arranging:
    a second inner shaft having a second fiber composite material in the proximal wire endpiece, and
    at least one protective layer enveloping the second inner shaft.

19. The method of claim 18, wherein in the second inner shaft in the proximal wire endpiece, a plurality of weakened sites are generated by mechanical interventions.

20. The method of claim 19, wherein the mechanical interventions include at least one of: buckling loads, bending loads, or breaking loads.

21. The method of claim 17, further comprising applying at least one marking element serving for marking purposes in an imaging method to an outer circumference of the first inner shaft.

22. The method of claim 21, further comprising applying the at least one marking element to at least one of: the distal wire endpiece or to the proximal wire endpiece.

23. The method of claim 17, wherein a bent shape is conferred on at least one of: the distal wire endpiece or to the proximal wire endpiece.

24. The method of claim 23, wherein the bent shape has a bending angle ($\alpha$) of at least 45° and at most 90°.

25. The method of claim 16, wherein for the mechanical interventions, the first inner shaft is placed over at least one mechanical edge and is subjected to a force acting transversely with respect to a longitudinal axis of an unweakened distal wire endpiece.

26. The method of claim 25, wherein the force is applied along the inner shaft at intervals of 1 mm to 3 mm.

27. The method of claim 16, wherein the mechanical interventions are carried out in at least two different rotation angle positions of the first inner shaft relative to a rotation about a longitudinal axis of the first inner shaft.

28. The method of claim 27, wherein the at least two different rotation angle positions of the inner shaft relative to a rotation about the longitudinal axis of the inner deviate from each other by 90°+/−10°.

29. The method of claim 16, wherein to generate the first inner shaft, a core made of the first fiber composite material is surrounded by at least one envelope layer made of a second fiber composite material, wherein fibers of the second fiber composite material are guided around the core with oppositely directed helical orientations.

30. The method of claim 29, wherein the first fiber composite material is different from the second fiber composite material.

31. The method of claim 16, wherein the first inner shaft is surrounded by at least one protective layer after the mechanical intervention.

32. The method of claim 31, wherein a protective jacket including PTFE, is shrink-fitted as the protective layer or, in a case of more than one protective layer, as an outermost protective layer.

33. A guidewire device for minimally invasive interventions, the guidewire device comprising:
    a wire main piece; and
    a distal wire endpiece adjoining the wire main piece, wherein:
        the distal wire endpiece includes an inner shaft and at least one protective layer enveloping the inner shaft,
        the inner shaft includes:
            a first fiber composite material,
            a plurality of weakened sites that are generated by mechanical interventions, a core, and
            an envelope layer surrounding the core,
        the core includes the first fiber composite material,
        the first fiber composite material includes glass fibers,
        the envelope layer includes a second fiber composite material, wherein the second fiber composite material includes aramid fibers being enveloped by a plastic matrix material, and
        the weakened sites are generated by at least one of: buckling loads, bending loads or breaking loads.

\* \* \* \* \*